United States Patent
Gremel et al.

(10) Patent No.: US 6,994,694 B2
(45) Date of Patent: Feb. 7, 2006

(54) APPARATUS FOR RETAINING CONCENTRIC PARTS WITHIN ONE ANOTHER

(75) Inventors: Robert F. Gremel, Huntington Beach, CA (US); Rowland W. Kanner, Guntersville, AL (US)

(73) Assignee: Saftey 1st Medical, Inc., Santa Ana, CA (US)

( * ) Notice: Subject to any disclaimer, the term of this patent is extended or adjusted under 35 U.S.C. 154(b) by 346 days.

(21) Appl. No.: 10/643,453

(22) Filed: Aug. 19, 2003

(65) Prior Publication Data

US 2005/0043688 A1    Feb. 24, 2005

(51) Int. Cl.
*A61M 5/32*    (2006.01)

(52) U.S. Cl. ...................... 604/192; 604/110
(58) Field of Classification Search ............. 604/192, 604/198, 110, 263, 164.08
See application file for complete search history.

(56) References Cited

U.S. PATENT DOCUMENTS

| | | | |
|---|---|---|---|
| 4,258,713 A * | 3/1981 | Wardlaw .................. 604/139 |
| 4,573,976 A | 3/1986 | Sampson et al. |
| 4,639,249 A * | 1/1987 | Larson .................... 604/198 |
| 4,643,199 A | 2/1987 | Jennings et al. |
| 4,655,751 A * | 4/1987 | Harbaugh ................. 604/198 |
| 4,666,435 A | 5/1987 | Braginetz |
| 4,737,144 A * | 4/1988 | Choksi ..................... 604/198 |
| 4,767,413 A * | 8/1988 | Haber et al. .............. 604/198 |
| 4,790,827 A * | 12/1988 | Haber et al. .............. 604/198 |
| 4,813,426 A | 3/1989 | Habner et al. |
| 4,871,355 A | 10/1989 | Kikkawa |
| 4,892,523 A | 1/1990 | Habner et al. |
| 4,911,693 A * | 3/1990 | Paris ....................... 604/192 |
| 4,935,016 A * | 6/1990 | Deleo ...................... 604/198 |
| 4,947,863 A * | 8/1990 | Haber et al. .............. 600/577 |
| 5,059,185 A | 10/1991 | Ryan |
| 5,067,945 A | 11/1991 | Ryan et al. |
| 5,106,379 A * | 4/1992 | Leap ....................... 604/198 |
| 5,116,326 A * | 5/1992 | Schmidt ................... 604/198 |
| 5,197,953 A * | 3/1993 | Colonna ................... 604/110 |
| 5,259,841 A * | 11/1993 | Hohendorf et al. ......... 604/110 |
| 5,290,256 A | 3/1994 | Weatherford et al. |
| 5,292,314 A * | 3/1994 | D'Alessio et al. .......... 604/198 |
| 5,352,208 A * | 10/1994 | Robinson .................. 604/198 |
| 5,433,712 A * | 7/1995 | Stiles et al. ............... 604/197 |
| 5,527,294 A | 6/1996 | Weatherford et al. |
| 5,961,473 A | 10/1999 | Fujii et al. |

* cited by examiner

*Primary Examiner*—Sharon Kennedy
(74) *Attorney, Agent, or Firm*—Walter A. Hackler

(57) ABSTRACT

Apparatus for retaining concentric parts within one another and enabling limited axial movement therebetween, includes an inner component having a shoulder disposed in an external perimeter thereof and an outer tubular component having a wall and an open end for receiving the inner component and an inner surface for abutting the shoulder and enabling a sliding interface therebetween. A retaining tab is provided and disposed in the wall proximate the open end for depression of a free end toward the wall and a slot formed in the wall beneath the tab enables the free end to be forced therepast for retaining the free end inside the wall for engagement with the shoulder, thus preventing separation of the inner component from the outer component.

18 Claims, 2 Drawing Sheets

APPARATUS FOR RETAINING CONCENTRIC PARTS WITHIN ONE ANOTHER

The present invention generally relates to apparatus for retaining concentric cylindrical parts and is more particularly directed to sharp devices requiring a shield such as, for example, shielded safety syringes and blood collection devices having an outer protective shield and a retractable needle.

Syringes are used for a variety of purposes and to avoid inadvertent contact with the needle, sleeves, or sheaths, have been provided for preventing inadvertent contact with the needle. In such devices, the needle is moveable to an axially extended position relative to the outer cylinder, or sleeve, for drawing a sample or giving an injection, to a retracted position, wherein the needle is completely surrounded and shielded by the protective sheath.

As hereinabove noted, this movement is such that a needle attached to the syringe can be extended outside the sheath for use as a typical syringe or retracted into the sheath, containing the sharp, hazardous point of the needle within the sheath, and thereby protecting healthcare professionals from secondary needle sticks. Typically, the syringe is retracted into the sheath by a spring.

The design of such a syringe and sheath combination must provide a method for retaining the syringe barrel within the safety sheath. It should be apparent that retention at one end of the sheath is accomplished by making the hole through which the needle protrudes smaller in diameter than the syringe barrel. Thus, the movement of the syringe past the bottom of the sheath is prevented.

The other, or top, end of the sheath must be sufficiently large to accommodate assembly of the syringe within the sheath. After the spring and syringe are disposed within the sheath, the syringe is retained therein by a retaining cleat. This cleat can be defeated by means of a trigger, thus allowing the needle to be extended.

However, the syringe also must be prevented from completely exiting the sheath.

The present invention provides for a molded lock mechanism for retaining the concentric sheath and syringe parts.

SUMMARY OF THE INVENTION

Apparatus in accordance with the present invention for retaining concentric parts within one another and enabling limited axial movement therebetween generally includes an inner component having a shoulder disposed on an external perimeter thereof and an outer tubular component having a wall, an open end receiving the inner component and an inner surface for abutting the shoulder and enabling the sliding interface therebetween.

A retaining tab is provided and disposed in the wall proximate the open end. The tab has one end attached to the wall, a free end and a body disposed generally parallel to a longitudinal axis of the outer component. The tab preferably has a suitable thickness for enabling depression of the free end toward the wall, and a slot formed in the wall beneath the tab is sized and disposed for enabling the free end to be forced therepast by depression of the tab as hereinabove noted.

In this position, the free end is disposed inside the wall for engagement with the shoulder, thus preventing separation of the inner component from the outer tubular component and accordingly, enabling limited axial movement therebetween.

In one embodiment of the present invention, the retaining tab extends downwardly from the open end with the free end disposed farther from the open end than the one end. In another embodiment of the present invention, the retaining tab extends upwardly toward the open end with the free end disposed closer to the open-end then the one end.

In the first embodiment, the free end has a tapered engagement surface for facilitating the free end to be forced past the slot end. The body may be rectangular to facilitate molding thereof and the tab is molded with the wall to provide for inexpensive manufacture.

The shoulder may comprise a ring surrounding the inner component, which may be molded therewith or an arcuate portion for engaging the tab.

In the second embodiment to the present invention, a tang may be provided and molded into the free end for engaging the slot end. Also in this embodiment, the free end includes an inside surface for engaging the shoulder and the tab is molded with the wall, as hereinabove noted to facilitate inexpensive manufacture.

More specifically, the inner component may comprise a syringe body and the outer tubular component may comprise a syringe sheath.

BRIEF DESCRIPTION OF THE DRAWINGS

The advantages and features of the present invention will be better understood by the following description when considered in conjunction with the accompanying drawings in which.

DETAILED DESCRIPTION

Figure 1:
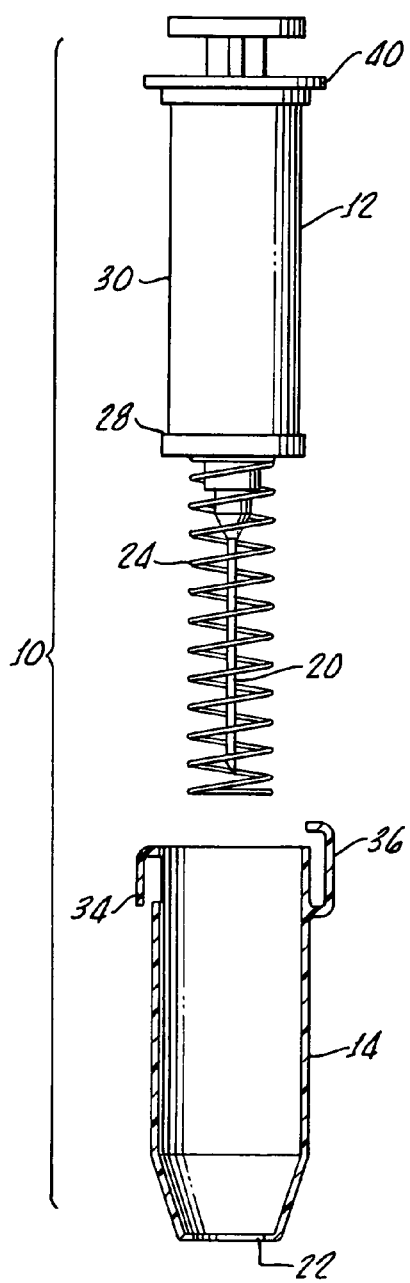
FIG. 1 is an exploded view of the apparatus in accordance with the present invention generally showing an inner component having a shoulder disposed on an external perimeter thereof, an outer tubular component having a wall with an open end for receiving the inner component, a spring and a retaining tab and slot for enabling limited axial movement between the inner component and outer component as hereinafter described.

With reference to FIG. 1, there is shown an apparatus 10 in accordance with the present invention for retaining parts, namely an inner component 12, which is preferably a syringe body or other suitable structure and an outer tubular component, which is preferably a sheath 14.

The syringe body 12 is moveable within the sheath 14 for extending a needle 20, or other sharp device, past an end 22 of the sheath in a conventional manner. A general description of shielded syringes is found in U.S. Pat. Nos. 5,290,256 and 5,527,294, which are to be incorporated herewith in their entirety for describing a syringe and sheath arrangement and concentric parts having axial movement therebetween.

As shown in FIGS. 1–5, the inner component 12 may include a shoulder 28 disposed on external perimeter 30 thereof. It should be appreciated that the shoulder 28 may comprise a ring extending around the component 12 or any partial circumference thereof, enabling engagement with a retaining tab 34, as here below described in greater detail. A latch 36 may be provided for engagement with a rim 40 of the syringe body 12 for maintaining an extended needle position past the syringe body 14 in a conventional manner.

The syringe body 12 and sheath 14 are preferably molded from suitable material for syringe application and the present invention provides for an inexpensive manufacture of the retaining apparatus, as hereinafter described.

Figure 2:
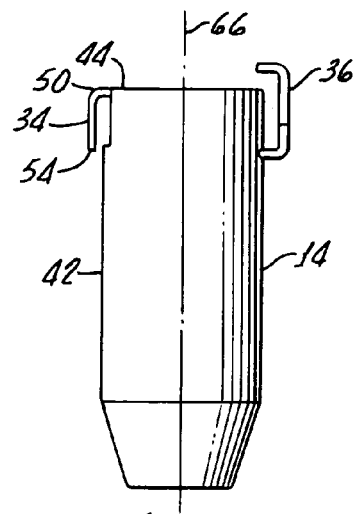
FIG. 2 is a plan view of an outer tubular component or syringe sheath in accordance to one embodiment of the present invention.
Figure 3:
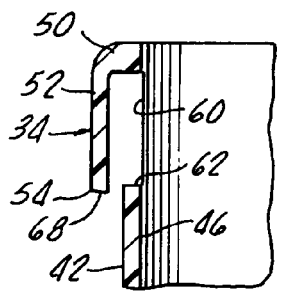
FIG. 3 is an exploded view of a retaining tab and slot as shown in FIG. 1 before movement of the tab toward a wall of the sheath component.
Figure 4:
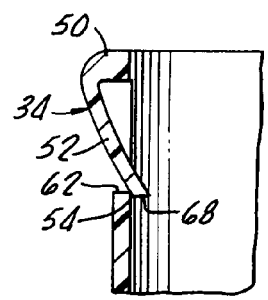
FIG. 4 is a view similar to that shown in FIG. 3 with a free end of the tab disposed within the wall for engagement with the inner component, or syringe body as shown in FIG. 1.

With reference now to FIGS. 2–5, the outer tubular component, or syringe sheath, 14 includes a wall 42 and an open end 44 for receiving an inner component 12, not shown in FIGS. 2–4, and an inner surface 46 for abutting the shoulder 28 and enabling a sliding interface therebetween.

Preferably, the tab 34 includes one end 50 molded with the component 14 having a generally rectangular body 52 and a free end 54. The body 52 may be rectangular in shape for facilitating molding and has a suitable thickness for enabling depression of the free end 54 toward the wall 42.

Figure 5:
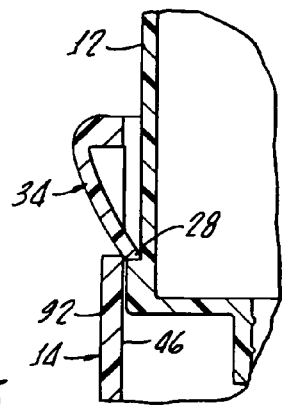
FIG. 5 is a cross sectional view showing engagement of a free end of the tab with the syringe body shoulder thus limiting removal of the syringe body from the sheath thereby enabling limited axial movement therebetween.
Figure 6:
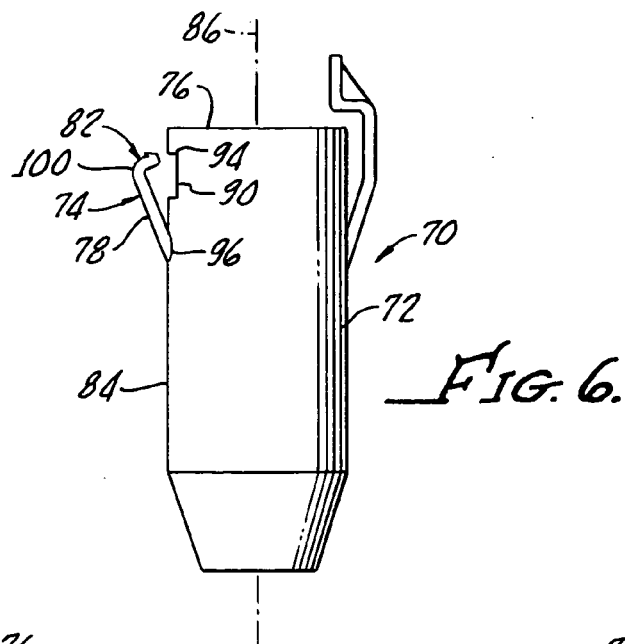
FIG. 6 is a plan view of an alternative embodiment of the present invention, in which the outer component, or syringe of the sheath includes a retaining tab extending upwardly toward an open end for engaging the syringe body shoulder shown in FIG. 1.
Figure 7:
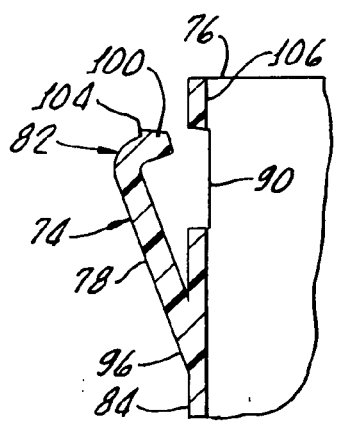
FIG. 7 is an enlarge cross sectional view of the retaining tab shown in FIG. 6.
Figure 8:
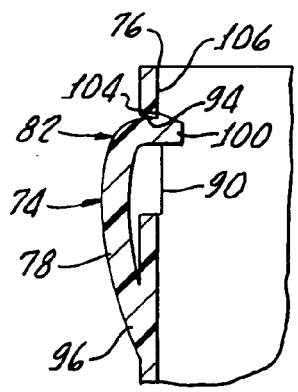
FIG. 8 is a view similar to that of FIG. 7 showing the tab being depressed or moved toward a wall of the sheath body and illustrating a tang for engaging an inside of the wall thereby preventing a shoulder of the syringe body to pass thereby.

A slot formed in the wall 42 beneath the tab 34 may be formed with an end 62 sized and disposed for enabling the free end 54 to be forced therepast by depression of the tab 34 in order to retain the free end 54 inside the wall 42, as shown in FIG. 4, for engagement with the shoulder 28, as shown in FIG. 5, thus preventing separation of the inner component or sheath body 12 from the outer tubular component 14, as shown in FIG. 5.

As shown in FIGS. 1–5, the retaining tab 34 extends downwardly from the open end 44 generally parallel to a longitudinal axis 66 and with the free end 54 disposed farther from the open end 44 than the end 50. In addition, the free end 54 has a tapered engagement surface 68 for facilitating and enabling the free end 54 to be forced past the slot end 62.

With reference now to FIGS. 6–9, there is shown an alternative embodiment 70 of an outer tubular component, or syringe body 72, having a retaining tab 74 disposed proximate an open end 76 and a body 78 generally disposed parallel to a longitudinal axis 80 and as hereinabove noted, having a suitable thickness for enabling depression of a free end 82 toward a wall 84 of the sheath 72.

A slot 90 and a wall 84 beneath a tab 74 includes an end 94 sized and disposed for enabling the free end 82 to be forced therepast by depression of tab 74.

An embodiment 70, the retaining tab 74 extends upwardly toward the open end 76 and the free end 82 is disposed closer to the open end 76 than an attached end 96, which is molded to the wall 84.

Figure 9:
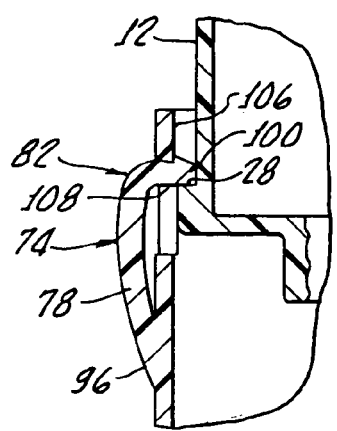
FIG. 9 is a view similar to FIG. 6 showing an engagement of the syringe body shoulder with an inside surface for engaging the shoulder.

In this embodiment 70, a tang is molded into the free end 82 for engagement with the slot end. A barb 104 may be provided for making positive engagement with an inside surface 106 of the wall 84, as shown in FIG. 9. The free end 82 includes an inside surface 108 for engaging the shoulder 28 of the syringe body 12, common reference characters illustrated in the FIGS. 6–9 corresponding to similar or identical structure to that shown in FIGS. 1–5.

Although there has been hereinabove described a specific apparatus for retaining concentric parts in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclose herein. Accordingly, any and all modifications, variations or equivalent arrangements which may occur to those skilled in the art, should be considered to be within the scope of the present invention as defined in the appended claims.

What is claimed is:

1. Apparatus for retaining concentric parts within one another and enabling limited axial movement therebetween, said apparatus comprising:

an inner component having a shoulder disposed on an external perimeter thereof;

an outer tubular component having a wall, an open end for receiving said inner component and an inner surface for abutting the shoulder and enabling a sliding interface therebetween;

a retaining tab disposed in the wall proximate the open end, the tab having one end attached to the wall, a free end and a body disposed parallel to a longitudinal axis of the outer component, said tab having suitable thickness for enabling depression of said free end toward the wall; and a slot formed in the wall beneath the tab, said slot having an end sized and disposed for enabling said free end to be forced therepast, by depression of the tab, in order to retain said free end inside the wall for engagement with said shoulder thus preventing separation of said inner component from said outer tubular component.

2. The apparatus according to claim 1 wherein said retaining tab extends downwardly from said open end with the free end disposed farther from said open end then said one end.

3. The apparatus according to claim 1 wherein said retaining tab extends upwardly toward said open end with the free end disposed closer to said open end then said one end.

4. The apparatus according to claim 2 wherein said free end has a tapered engagement surface for facilitating the free end to be forced past the slot end.

5. The apparatus according to claim 4 wherein the tab body is rectangular.

6. The apparatus according to claim 4 wherein said tab is molded with said wall.

7. The apparatus according to claim 2 wherein said shoulder comprises a ring surrounding said inner component.

8. The apparatus according to claim 7 wherein said ring is molded with said inner component.

9. The apparatus according to claim 3 further comprises a tang molded into said free end for engaging the slot end.

10. The apparatus according to claim 9 wherein said free end includes an inside surface for engaging said shoulder.

11. The apparatus according to claim 10 wherein the tab body is rectangular.

12. The apparatus according to claim 9 wherein said tab is molded with said wall.

13. The apparatus according to claim 3 wherein said shoulder comprises a ring surrounding said inner component.

14. The apparatus according to claim 3 wherein said ring is molded with said inner component.

15. Apparatus for retaining concentric parts within one another and enabling limited axial movement therebetween, said apparatus comprising:
   a syringe body having a shoulder comprising a ring molded with an external perimeter thereof;
   a syringe sheath having a wall, an open end for receiving said syringe body and an inner surface for abutting the shoulder and enabling a sliding interface therebetween;
   a retaining tab disposed in the wall proximate the open end, the tab having one end molded with the wall, a free end and a rectangular body disposed parallel to a longitudinal axis of the syringe sheath, said tab having suitable thickness for enabling depression of said free end toward the wall; and
   a slot formed in the wall beneath the tab, said slot having an end sized and disposed for enabling said free end to be forced therepast, by depression of the tab, in order to retain said free end inside the wall for engagement with said shoulder thus preventing separation of said syringe body from said syringe sheath.

16. The apparatus according to claim 15 wherein said retaining tab extend downwardly from said open end with the free end is disposed father from said open end then said use end.

17. Apparatus for retaining concentric parts within one another and enabling limited axial movement therebetween, said apparatus comprising:
   a syringe body having a shoulder comprising a ring molded with an external perimeter thereof;
   a syringe sheath having a wall, an open end for receiving said syringe body and an inner surface for abutting the shoulder and enabling a sliding interface therebetween;
   a retaining tab disposed in the wall proximate the open end, the tab having one end molded with the wall, a free end and a rectangular body disposed parallel to a longitudinal axis of the syringe sheath, said tab having suitable thickness for enabling depression of said free end toward the wall, said free end including an inside surface for engaging said shoulder;
   a slot formed in the wall beneath the tab, said slot having an end sized and disposed for enabling said free end to be forced therepast, by depression of the tab, in order to retain said free end inside the wall for engagement with said shoulder thus preventing separation of said inner component from said outer tubular component; and
   a tang molded into said free end for engaging the slot end.

18. The apparatus according to claim 17 wherein said retaining tab extends upwardly toward said open end with the free end disposed closer to said open end then said one end.

* * * * *